(12) United States Patent
Kharazi et al.

(10) Patent No.: US 9,080,184 B2
(45) Date of Patent: Jul. 14, 2015

(54) TRANSGENIC THERAPEUTIC STEM CELLS AND METHODS FOR THEIR USE AND MANUFACTURE

(71) Applicants: Alex Kharazi, San Diego, CA (US); M G Muralidhar, Poway, CA (US); Grigory Vertelov, San Diego, CA (US)

(72) Inventors: Alex Kharazi, San Diego, CA (US); M G Muralidhar, Poway, CA (US); Grigory Vertelov, San Diego, CA (US)

(73) Assignee: Stemedica Cell Technologies, Inc., San Diego, CA (US)

( * ) Notice: Subject to any disclaimer, the term of this patent is extended or adjusted under 35 U.S.C. 154(b) by 0 days.

(21) Appl. No.: 13/776,614

(22) Filed: Feb. 25, 2013

(65) Prior Publication Data

US 2014/0242047 A1    Aug. 28, 2014

(51) Int. Cl.
| | | |
|---|---|---|
| *A61K 48/00* | (2006.01) | |
| *C12N 15/63* | (2006.01) | |
| *C07H 21/04* | (2006.01) | |
| *C12N 15/85* | (2006.01) | |
| *C12N 5/16* | (2006.01) | |

(52) U.S. Cl.
CPC ............... *C12N 15/85* (2013.01); *C07H 21/04* (2013.01); *C12N 5/16* (2013.01); *C12N 15/63* (2013.01)

(58) Field of Classification Search
CPC .......... C12N 5/16; C12N 15/63; C12N 15/85; C07H 21/04
USPC ..................... 424/93.21; 435/320.1; 536/23.5
See application file for complete search history.

(56) References Cited

U.S. PATENT DOCUMENTS

2006/0035373 A1 *    2/2006   Zhang et al.

OTHER PUBLICATIONS

Han et al., 2007, Journal Korean Medical Science, vol. 22, p. 242-247.*

* cited by examiner

*Primary Examiner* — Shin Lin Chen
(74) *Attorney, Agent, or Firm* — Harris F. Brotman

(57) ABSTRACT

The invention relates to transgenic stem cells for therapeutic use. Stem cells according to the invention comprise at least one therapeutic trans gene that is expressed when transplanted to a subject. Methods of use and manufacturing the transgenic stem cells of the invention are also contemplated, including the use of transiently transgenic G-CSF bone marrow stem cells for treating the penumbra of ischemic tissues such as central nervous system tissues.

1 Claim, 8 Drawing Sheets

CONTROL					G-CSF TRANSFECT

CONTROL                    G-CSF TRANSFECT

CONTROL                    G-CSF TRANSFECT

TRANSGENIC THERAPEUTIC STEM CELLS AND METHODS FOR THEIR USE AND MANUFACTURE

CROSS-REFERENCE TO RELATED APPLICATIONS

This application claims priority to provisional application Ser. No. 61/603,214, filed Feb. 24, 2012, the entire contents of which are incorporated herein by reference in their entirety.

BACKGROUND

The invention generally relates to stem cells and therapeutic uses thereof. More particularly, the invention relates to transgenic stem cells that have been genetically modified with an exogenous polynucleotide. The use of transgenic stem cells for the treatment of medical conditions defined by an ischemic penumbra are within the scope of the invention.

In pathology and anatomy the penumbra is the area surrounding an ischemic event such as an ischemic, thrombotic or embolic stroke. Immediately following the event, blood flow and therefore oxygen transport is reduced locally, leading to hypoxia of the cells near the location of the original insult. This can lead to cell death and amplify the original damage from the infarction, however, the penumbra area may remain viable after an ischemic event due to the collateral arteries that supply the penumbral zone.

As time elapses after the onset of stroke, the extent of the penumbra tends to decrease (*British Medical Bulletin*, 65 (1), 145-157). Without relying on any scientific principal or theory, the existence of a penumbra implies that salvage of the cells is possible. There is a high correlation between the extent of spontaneous neurological recovery and the volume of penumbra that escapes infarction; therefore, saving and restoring the function the penumbra should improve the clinical outcome.

One widely accepted definition for penumbra describes the area as "ischemic tissue potentially destined for infarction but not yet irreversibly injured and the target of acute therapies" (*Stroke* 32: 2657). The original definition of the penumbra referred to areas of the brain that were damaged but not yet dead, and offered promise to rescue the brain tissue with the appropriate therapies (*Nature Medicine* 14 (5): 497-500).

What is needed in the art therefore is a method and composition for rescuing the ischemic penumbra thereby providing enhanced tissue regeneration and recovery outcomes for a variety of ischemic conditions, including, but not limited to stroke, myocardial infarction, retinal ischemia, pancreatic ischemia and ALS.

SUMMARY OF THE INVENTION

The invention relates to transgenic stem cells for therapeutic use. Stem cells according to the invention comprise at least one therapeutic trans gene, such as granulocyte colony stimulating factor (G-CSF) that is expressed when transplanted to a subject. Methods of use and manufacturing the transgenic stem cells of the invention are also contemplated, including the use of transiently transgenic G-CSF bone marrow stem cells for treating the penumbra of ischemic tissues such as central nervous system tissues.

An object of the invention is to provide a composition of transgenic stem cells comprising an exogenous polynucleotide that encodes G-CSF.

A further object of the invention is to provide a composition of transgenic stem cells comprising an exogenous polynucleotide that encodes G-CSF, wherein said transgenic stem cell is transiently transfected with G-CSF.

A further object of the invention is to provide a composition of transgenic mesenchymal stem cells comprising an exogenous polynucleotide that encodes G-CSF, wherein said transgenic mesenchymal stem cells are transiently transfected with G-CSF and said polynucleotide is in contact with a microcarrier.

A further object of the invention is to provide a composition of transgenic mesenchymal stem cells that comprise an exogenous polynucleotide that encodes G-CSF, wherein said mesenchymal stem cells are grown under low oxygen conditions.

A further object of the invention is to provide a composition of transgenic mesenchymal stem cells that comprise an exogenous polynucleotide that encodes G-CSF, wherein said transgenic mesenchymal stem cells are grown under low oxygen conditions and are positive for at least one of CD13, CD29, CD73, CD81, CD90, CD105, CD164 and CD166, and negative for at least one of CD14, CD19, CD34, CD45, CD122 and HLA-DR.

A further object of the invention is to provide a composition of transgenic mesenchymal stem cells that comprise an exogenous polynucleotide that encodes G-CSF, wherein said transgenic mesenchymal stem cells are grown under low oxygen conditions and are positive for CD13, CD29, CD73, CD81, CD90, CD105, CD164 and CD166, and negative for CD14, CD19, CD34, CD45, CD122 and HLA-DR.

A further object of the invention is to provide a method of treating the penumbra of an ischemic tissue in a subject in need thereof comprising administering to said subject a composition of transgenic stem cells that express an exogenous polynucleotide that encodes G-CSF.

A further object of the invention is to provide a method of treating the penumbra of an ischemic tissue in the central nervous system of a subject in need thereof comprising administering to said subject a composition of transgenic stem cells that express an exogenous polynucleotide that encodes G-CSF.

A further object of the invention is to provide a method of treating the penumbra of an ischemic tissue in the central nervous system of a subject in need thereof comprising administering to said subject a composition of transgenic mesenchymal stem cells that express an exogenous polynucleotide that encodes G-CSF, wherein said mesenchymal stem cells are grown under low oxygen conditions and are positive for CD13, CD29, CD73, CD81, CD90, CD105, CD164 and CD166, and negative for CD14, CD19, CD34, CD45, CD122 and HLA-DR.

DEFINITIONS

Figure 1:
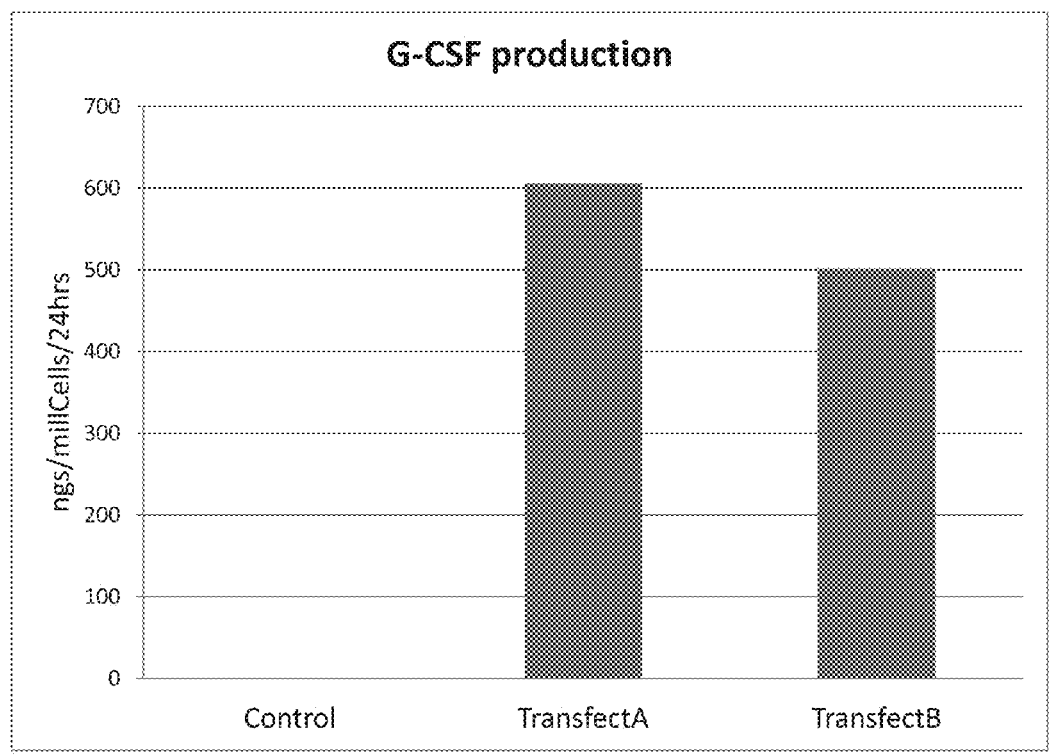
FIG. 1 shows the in vitro expression of G-CSF by transgenic mesenchymal stem cells.

The term "stem cell" refers to an undifferentiated cell which has the ability to both self-renew (through mitotic cell division) and undergo differentiation to form a more specialized cell. Stem cells have varying degrees of potency. A precursor cell is but one example of a stem cell.

"Differentiation" refers to the biological process by which a less specialized cell becomes a more specialized cell type. For example, during embryonic development, pluripotent embryonic stem cells "differentiate" to form multipotent mesenchymal, ectodermal and endodermal stem cells, each of which are limited to a specific developmental pathway (i.e. range of tissues).

"Differentiation potential," "cell potential," "plasticity" and "potential" are used interchangeably herein to refer to the ability of a stem cell to differentiate into one or more specialized cell types.

"Mesenchymal cells," are mesodermal germ lineage cells which may or may not be differentiated. The mesenchymal cells of the invention include cells at all stages of differentiation beginning with multipotent mesenchymal stem cells, down to fully differentiated terminal cells.

"Ectodermal cells," are ectodermal germ lineage cells which may or may not be differentiated. The ectodermal cells of the invention include cells at all stages of differentiation beginning with multipotent ectodermal stem cells, down to fully differentiated terminal cells.

"Endodermal cells," are endodermal germ lineage cells which may or may not be differentiated. The endodermal cells of the invention include cells at all stages of differentiation beginning with multipotent endodermal stem cells, down to fully differentiated terminal cells.

The terms "purified" and "isolated" when used to refer to a cell population (e.g. composition of cells) means the cells in the population are essentially free from cells of a different type. A composition of cells is considered "purified," or "substantially purified," if it contains at least about 75%, at least about 80%, at least about 85%, at least about 90%, at least about 95% or at least about 100% of a desired type.

A "functional fragment" is a portion of a polypeptide or nucleic acid molecule that is of a length sufficient to have at least one biological activity attributed to the polypeptide or nucleic acid molecule from which the fragment is derived. Exemplary biological activities of a therapeutic polypeptide include reducing apoptosis, increasing angiogenesis, or increasing proliferation of a cell of interest.

By the term "vector" is meant a recombinant plasmid or viral construct used as a vehicle to introduce one or more transgenes into a cell. Preferred vectors for in vivo use in subjects are viral vectors, and as discussed, particularly preferred viral vectors are rAAV vectors. As used herein, vector is a term referring to a sequence of genetic material into which a nucleotide sequence (or "transgene," typically a fragment of DNA encoding a polypeptide of interest) has been inserted and which can be used to introduce exogenous genetic material into a cell or into the genome of an organism. An "expression vector" is vector used to introduce a DNA or RNA sequence into a cell, causing the product of the DNA or RNA (typically a protein or polypeptide) to be produced by the cell.

The term "transient transfection" refers to a transfection process wherein the exogenous polynucleotide (i.e. trans gene) is not integrated into the nuclear genome such that the exogenous polynucleotide may be diluted through mitosis or degraded.

The term "stable transfection" refers to a transfection process wherein the transfected gene remains in the genome of the cell and its daughter cells.

The term "patient," or "subject," refers to animals, including mammals, preferably humans, who are treated with the pharmaceutical compositions or in accordance with the methods described herein.

The term "pharmaceutically acceptable carrier" (or medium), which may be used interchangeably with the term "biologically compatible carrier" (or medium), refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

A "central nervous system disorder," or "CNS disorder," refers to a condition or injury that impairs the normal function of the mammalian central nervous system, such as, for example, neurodegenerative disorders, traumatic injuries (to the brain or spinal cord) and CNS dysfunctions. Neurodegenerative CNS disorders are generally associated with a prolonged deterioration of CNS neural tissue including, but not limited to, Alzheimer's disease, Parkinson's disease, multiple sclerosis (MS), Huntington's disease, amyotrophic lateral sclerosis, cerebral palsy, Gaucher's disease, Tay-Sachs disease, Niemann Pick's disease, sphingomyelin lipidoses, and brain tumors. CNS disorders further include traumatic injuries, such as for example, hemorrhagic stroke, ischemic stroke, and mechanical injuries to the brain and spinal cord. The phrase "CNS disorder" further includes dysfunctions such as, for example, depression, epilepsy, and schizophrenia.

The term "ischemia" refers to local anemia due to mechanical obstruction of the blood supply. "Ischemic" refers to a tissue that has been damaged by ischemia.

The term "stroke" refers to a condition wherein the blood flow to the brain stops or is restricted to the point of causing an impairment of neurological function. The term "stroke" includes ischemic stroke, which may be caused by an obstruction that blocks a blood vessel or artery in the brain, and hemorrhagic stroke which may be caused when a blood vessel in the brain ruptures and spills blood into the surrounding tissue.

The term "CNS ischemia," as used herein, is intended to refer to the partial or complete reduction of blood flow to one or more areas of the brain or spinal cord. The ischemia can be global, e.g. a generalized reduction in blood flow due to systemic hypotension, or focal, e.g. due to a disease in one or more cerebral arteries or localized trauma. The ischemia may be the result of stenosis or occlusion of a blood vessel, for example due to a thrombosis, an embolism, or particle.

As used herein, a "therapeutically amount" refers to the number of transplanted cells which are required to produce a therapeutic effect for the disorder which is being treated. For example, where the treatment is for Parkinsonism, transplantation of a therapeutically effective amount of cells will typically produce a reduction in the amount and/or severity of the symptoms associated with that disorder, e.g., rigidity, akinesia and gait disorder.

As used herein, "treating a host," or "treatment," includes prophylactic, palliative, and curative intervention in a disease process. Thus, the term "treatment" as used herein, typically refers to therapeutic methods for reducing or eliminating the symptoms of the particular disorder for which treatment is sought. The term "host," as used herein, generally refers to any warm blooded mammal, such as humans, non-human primates, rodents, and the like, which is to be the recipient of the particular treatment. The terms "host," "patient" and "subject" are used interchangeably.

DETAILED DESCRIPTION

The invention relates to stem cells that are modified to express at least one exogenous polynucleotide, and methods for making and using such stem cells in a variety of therapeutic applications. More particularly, the invention relates to stem cells that are transgenic for a therapeutic gene, such as G-CSF, and methods for using such stem cells for treatment of the penumbra of ischemic tissues.

In some aspects of the invention, mesenchymal stem cells are transfected with an exogenous polynucleotide (e.g. G-CSF). Mesenchymal stem cells for use with the invention include any mesodermal germ lineage cell. Such mesodermal stem cells may be derived from any mesodermal tissue source that provides a stem cell capable of producing daughter cells that form differentiated cells of at least one germ lineage. Suitable sources of mesodermal cells for practicing the invention include, but are not limited to bone marrow, blood (peripheral blood), dermis, periosteum, synovium, peripheral blood, skin, hair root, muscle, uterine endometrium, adipose, placenta, menstrual discharge, chorionic villus, amniotic fluid, umbilical cord blood, umbilical cord blood, and combinations thereof.

Mesenchymal stem cell compositions for use with the invention may comprise purified or non-purified mesenchymal stem cells. Mesenchymal stem cells for use with the invention, and methods of their manufacture, include those disclosed in the following references, the disclosures of which are incorporated herein by reference: U.S. Pat. No. 5,215,927; U.S. Pat. No. 5,225,353; U.S. Pat. No. 5,262,334; U.S. Pat. No. 5,240,856; U.S. Pat. No. 5,486,359; U.S. Pat. No. 5,759,793; U.S. Pat. No. 5,827,735; U.S. Pat. No. 5,811,094; U.S. Pat. No. 5,736,396; U.S. Pat. No. 5,837,539; U.S. Pat. No. 5,837,670; U.S. Pat. No. 5,827,740; U.S. Pat. No. 6,087,113; U.S. Pat. No. 6,387,367; U.S. Pat. No. 7,060,494; Jaiswat, N., et al., J. Cell Biochem. (1997) 64(2): 295 312; Cassiede P., et al., J. Bone Miner. Res. (1996) 11(9): 1264 1273; Johnstone, B., et al., (1998) 238(1): 265 272; Yoo, et al., J. Bone Joint Sure. Am. (1998) 80(12): 1745 1757; Gronthos, S., Blood (1994) 84(12): 41644173; Basch, et al., J. Immunol. Methods (1983) 56: 269; Wysocki and Sato, Proc. Natl. Acad. Sci. (USA) (1978) 75: 2844; and Makino, S., et al., J. Clin. Invest. (1999) 103(5): 697 705.

In an aspect of the invention, stromal mesenchymal stem cells are modified to express a polynucleotide (or active fragment thereof). Such stromal cells may be identified by their cell surface expression profile. In one aspect of the invention, mesenchymal stem cells are selected based on a cell surface marker expression profile, wherein the cells are positive for at least one of CD13, CD29, CD73, CD81, C90, CD105, CD164, CD166, and negative for at least one of CD14, CD19, CD34, CD45, CD122, and HLA-DR. Embodiments of transgenic stromal mesenchymal stem cells "Stemedica MSC," or "sMSC") include those with the following cell marker profile: CD13+, CD29+, CD73+, CD81+, CD90+, CD105+, CD164+, CD166+, CD14−, CD19−, CD34−, CD45−, CD122−, and HLA-DR−, sMSC may be obtained by culturing stromal MSC under low oxygen conditions beginning with passage 1 and purifying them using any marker-based selection method such as magnetic bead sorting and/or FACS. sMSC have unique biological and physical characteristics beyond their marker profile. For example, sMSCs have a doubling time of about 23 hours when grown under low oxygen conditions.

In some aspects of the invention, stem cells are grown under low oxygen conditions. As used herein, the term "low oxygen" refers to culture conditions in which the ambient oxygen concentration is less than atmospheric oxygen concentrations at sea level. Low oxygen conditions generally means any oxygen concentration below about 20%, preferably below about 15%, more preferably below about 5-10%, at sea level. Low oxygen conditions may be kept as close as possible to the normal physiological oxygen conditions in which a particular stem cell would be found in vivo. Thus, in some embodiments, the conditions employed for cells will depend on the regional origin of a particular cell; such conditions are known to the skilled artisan, "Physiologic" oxygen levels are the range of oxygen levels normally found in healthy tissues and organs.

In one embodiment, the low ambient oxygen conditions comprise an ambient oxygen condition of between about 0.25% to about 18% oxygen. In another embodiment, the ambient oxygen conditions comprise an ambient oxygen condition of between about 0.5% to about 15% oxygen. In still another embodiment, the low ambient oxygen conditions comprise an ambient oxygen condition of between about 1% to about 10% oxygen. In further embodiments, the tow ambient oxygen conditions comprise an ambient oxygen condition of between about 1.5% to about 6% oxygen. Of course, these are exemplary ranges of ambient oxygen conditions to be used in culture and it should be understood that those of skill in the art will be able to employ oxygen conditions falling in any of these ranges generally or oxygen conditions between any of these ranges that mimics physiological oxygen conditions for the particular cells. Thus, one of skill in the art could set the oxygen culture conditions at 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, or any other oxygen condition between any of two of these concentrations.

One aspect of the invention relates to the timing (e.g. stage of cell culture) at which the stem cells are exposed to low oxygen conditions. Stem cells may be exposed to reduced oxygen tension at any time during the in vitro culture of the stem cells. Stem cells may be exposed to reduced oxygen tension at times including, but not limited to, after collection of the stem cells as a tissue sample, during disaggregation of such tissue sample, during the primary culture of stem cells, during the in vitro expansion of the stem cells (e.g. over multiple cell passages), during priming (e.g. when stem cells are induced to assume a desired biological activity prior to injection into a subject), and combinations thereof.

The stem cells of the invention are transgenic for at least one exogenous polynucleotide. Such exogenous polynucleotides may encode proteins that are therapeutic in the treatment of a medical condition, such as treating the penumbra of an ischemic tissue, for example. In a preferred embodiment, the at least one exogenous polynucleotide comprises G-CSF. Other non-limiting polynucleotides for use with the invention include, but are not limited to, acidic and basic fibroblast growth actors (aFGF and bFGF), vascular endothelial growth factor (VEGF-1), VEGF165, epidermal growth factor (EGF), transforming growth factor .alpha. and .beta. (TGF-.alpha. and TFG-.beta.), platelet-derived endothelial growth factor (PD-ECGF), platelet-derived growth factor (PDGF), tumor necrosis factor .alpha. (TNF-.alpha.), hepatocyte growth factor (HGF), insulin like growth factor (IGF-1, IGF-2), erythropoietin, colony stimulating factor (CSF), macrophage-CSF (M-CSF), granulocyte/macrophage CSF (GM-CSF), angiopoetin-1 (Ang1) and nitric oxide synthase (NOS), and functional fragments thereof, and combinations thereof.

The stem cells of the invention may be modified to express one or more exogenous polynucleotides (e.g. G-CSF) using any method that achieves expression of the polynucleotides in vitro and/or in the body of a subject. Such genetic modification may be accomplished by transfection or transduction. As used herein, the term "transfection" refers to a process of delivering heterologous DNA, such as a viral vector encoding a transgene of interest, or plasmid DNA to a cell by physical or chemical methods. Stem cells of the invention may be transiently or stably transfected. Use of the term "transduction" refers to the process whereby foreign DNA is introduced into another cell via a viral vector.

In a preferred embodiment, stem cells are transiently transfected with the polynucleotide of interest. Methods for transiently transfecting the stem cells of the invention include, but are not limited to, electroporation, chemical transfection (e.g. calcium phosphate precipitation), microcarriers (e.g. gene gun), and combinations thereof. In a preferred embodiment, stem cells of the invention are transiently transfected via microcarriers (e.g. cationic polymers). In such embodiments, transgenes carried by the transgenic stem cells of the invention can be expressed for extended periods in vivo (e.g. from about 12 hours to at least several months) after transplantation to a host.

In some aspects of the invention, stem cells are transduced to express an exogenous polynucleotide. Suitable methods for transducing stem cells according the invention are known in the art and include, but are not limited to, U.S. Published Application No. 20100028312.

In some aspects of the invention, transgenic stem cells (e.g. transgenic mesenchymal stem cells) are used to treat the penumbra of an ischemic tissue. As used herein, the term "penumbra," or "ischemic penumbra," refers to an area of moderately ischemic tissue surrounding an area of more severe ischemia (i.e. zone of dead or necrotic cells) (*Nature Medicine* 14 (5): 497-500). The penumbra therefore is defined by a zone of cells that are damaged but not yet dead and which may have a blood flow below 20 mL/100 g/min (*Neurology* 31 (3): 44-6). Although the ischemic penumbra is classically associated with ischemia of the brain and central nervous system, the term penumbra as used herein may include any moderately ischemic region surrounding an area of severe (i.e. necrotic) ischemic tissue including, but not limited to, myocardium damaged by myocardial infarction, retinal tissue damaged by retinal ischemia, kidney tissue damaged by kidney infarction, pancreatic tissue damaged by pancreatic infarction, and central nervous system tissue damaged by ALS.

Without being limited to any particular theory or mechanism, the administration of transgenic stem cells according to the invention treats the ischemic penumbra by preventing or inhibiting further ischemic damage to the cells of the penumbra, repairing the cells of the penumbra, restoring the function of the cells of the penumbra, regenerating the region of severe ischemia (i.e. necrotic tissue), restoring or improving blood flow and/or angiogenesis (i.e. perfusion) in the penumbra and/or the severe ischemic region, and combinations thereof. In one aspect of the invention, the administration of therapeutic transgenic stem cells restores the function of the penumbra of ischemic neural tissue following ischemic stroke. In a preferred embodiment, such transgenic stem cells comprise low oxygen stromal bone marrow stem cells (e.g. sMSCs) that are modified (e.g. transiently transfected) to express G-CSF.

In some aspects, the invention's stem cell compositions are made by suspending an appropriate amount of transgenic stem cells in a pharmaceutically acceptable carrier. As used herein the phrase "pharmaceutically acceptable" means the carrier, or vehicle, does not cause an adverse reaction when administered to a mammal. Such carriers are non-toxic and do not create an inflammatory or anergic response in the body. Pharmaceutically acceptable carriers for practicing the invention include any of the well known components useful for immunization such as, for example, culture media and phosphate buffered saline. Additional physiologically acceptable carriers and their formulations are well-known and generally described in, for example, Remington's Pharmaceutical Science (18.sup.th. Ed., ed. Getmaro, Mack Publishing Co., Easton, Pa., 1990) and the Handbook of Pharmaceutical Excipients (4.sup.th ed., Ed. Rowe et al, Pharmaceutical Press, Washington, D.C.), each of which is incorporated by reference One aspect of the invention relates to the concentration of cells that are administered to a subject. In this regard, transgenic stem cells may be administered at any concentration that provides a therapeutic effect when administered according to the methods disclosed herein. Suitable stem cell concentrations range between about $10^4$ to about $10^7$ cells/ml. The concentration of cells used for a particular treatment takes into consideration such factors as viscosity restrictions imposed by the diameter of the needle used for injection, as well as the volume of the compositions that are used for treatment. Transgenic stem cells may be administered in a single injection, multiple simultaneous injections or multiple sequential injections at the same or different injection sites. Administration may also take on any route that treats an ischemic penumbra, such routes including, but not limited to, intra-arterial, intramuscular, intraperitoneal, subcutaneous, intramuscular, intraabdominal, intraocular, retrobulbar, intranasal, intrathecal, intracranial and combinations thereof.

Example 1

Stem Cell Transfection

Clinical grade bone marrow aspirate was purchased from Lonza. The mononuclear cells were isolated from fresh specimen using Histopaque and seeded into Petri dishes. The cells were expanded in DMEM/F12 medium containing FGF-2 and 15% bovine growth serum (BGS) at 37° C. in the 5% CO2 incubator under 5% oxygen conditions. Passage 3 cells were harvested with Trypsin and centrifuged to form a pellet. The medium was removed and the cells resuspended in PBS. The number of cells was determined and the cell suspension centrifuged. The PBS was removed and the cells were resuspended in electroporation buffer containing 50 ug/ml plasmid DNA such that the cell suspension contained $5 \times 10^6$ cells/100 uls. The cells were electroporated using a Neon electroporation device according to manufacturer's instructions with a pulse of 1200V for 30 ms.

The cells were transferred to a tube containing growth medium, mixed well and centrifuged. The medium was removed and the cell pellet resuspended in Cryostor. The cells were transferred to a cryotube and frozen at −80° C. overnight. These were then transferred to liquid nitrogen for long term storage.

The cells were thawed and growth medium added slowly to prevent osmotic shock. After centrifugation and re-suspension in growth medium, the cell count and viability were determined. Cells were cultured in tissue culture dishes and supernatants harvested 24 hrs post-seeding. The amount of G-CSF was measured by Elisa and normalized to amount secreted by a million cells in 24 hrs.

The control group comprised non-transfected hMSC. There was substantial human G-CSF production in the transfected cells of the two identical experimental groups (Transfect A and Transfect B). The graph in FIG. 1 represents typical G-CSF amounts in the supernatants of cells 24 hrs post-culturing.

toxicity. On this basis, we chose 4×/5×LTX, 0.4×/0.5× Sterrifect and 0.1/0.2× hESC as the preferred ratios for optimal transfection.

Figure 3A:
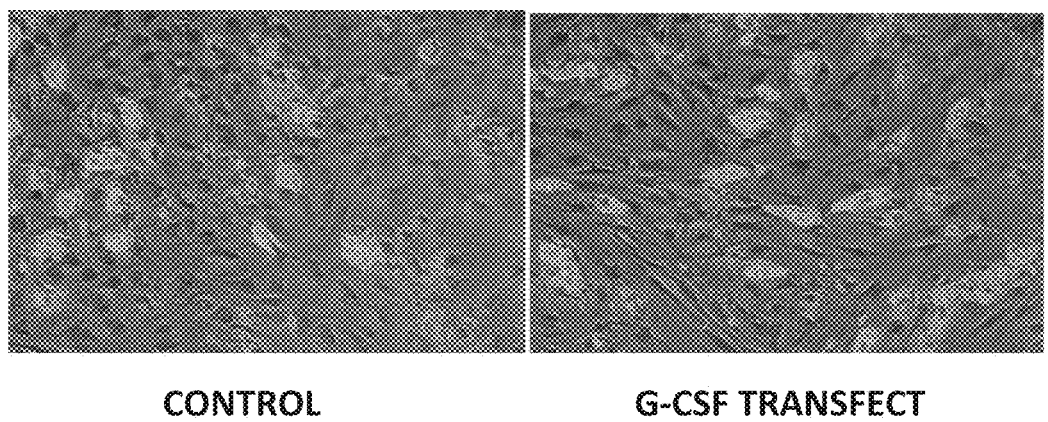
FIGS. 3A-C show the differentiation potential of transgenic bone marrow mesenchymal cells.
Figure 3B:
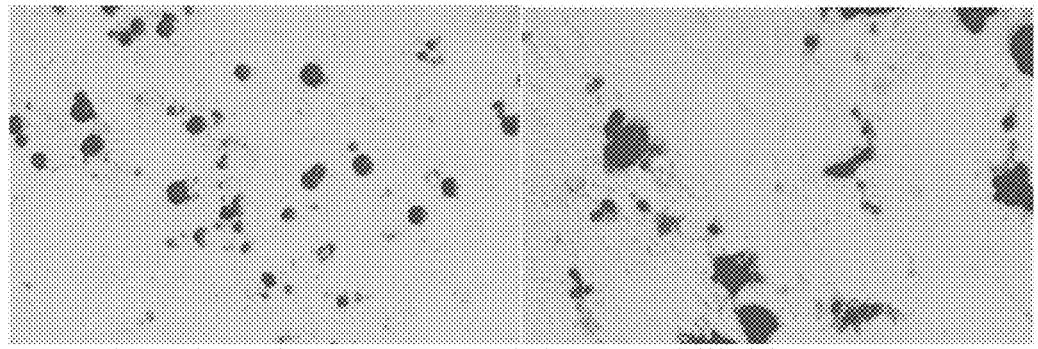
Figure 3C:
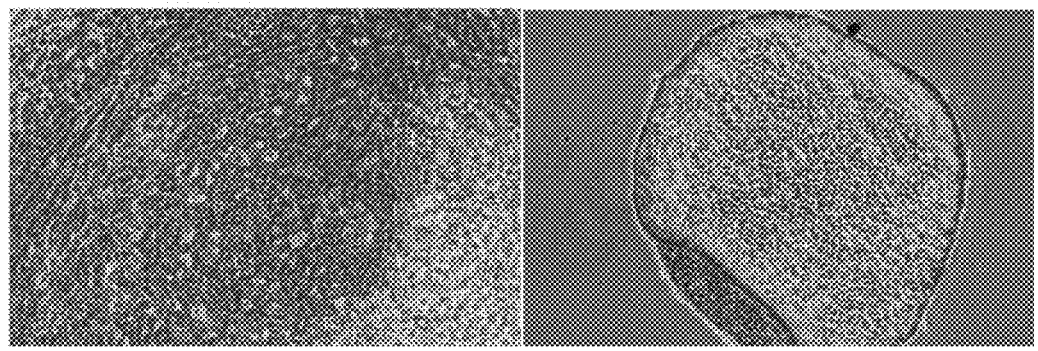
Figure 4:
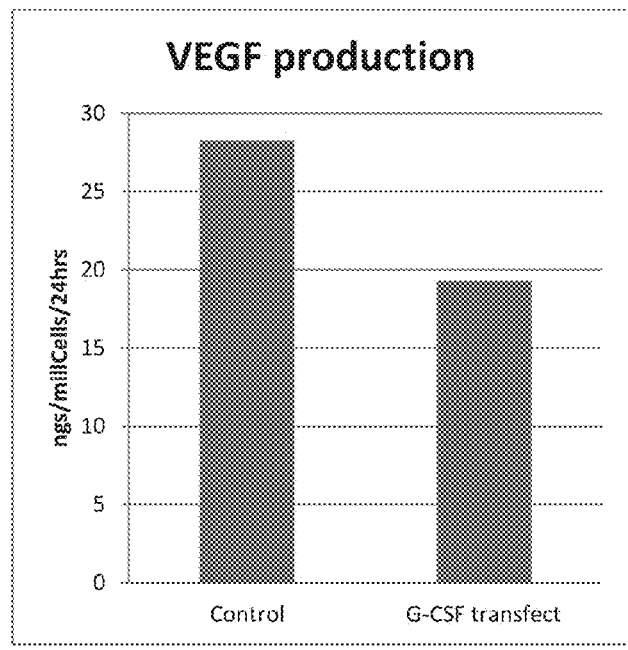
FIG. 4 shows the expression of VEGF by transgenic mesenchymal stem cells.

Next, we acquired a plasmid with the human G-CSF cDNA under the control of CMV promoter (Origene). This plasmid was used to force G-CSF expression in hMSCs. Cells were seeded and grown to about 50% confluency and transfected by electroporation as above. The supernatants from transfected cells were harvested 24 hrs post-transfection and the amounts of secreted G-CSF protein determined by ELISA. We were able to achieve G-CSF secretion. The in vitro testing of transfected MSC demonstrated that they express all appropriate markers (Table 1 below). The transfected cells preserved their multipotency and demonstrated adipocyte (FIG. 3A), osteocyte (FIG. 3B) and chondrocyte differentiation (FIG. 3C). The transfected cells also maintained their VEGF secretion as shown in FIG. 4.

TABLE 1

| Marker | CD73 | CD90 | CD105 | CD166 | CD14 | CD19 | CD34 | CD45 | HLA-DR |
|---|---|---|---|---|---|---|---|---|---|
| Control | 100% | 100% | 100% | 100% | 0% | 0% | 0% | 0% | 3% |
| G-CSF transfects | 100% | 100% | 100% | 100% | 0% | 0% | 0% | 0% | 3% |

Example 2

Transient Stem Cell Transfection

The purpose of these experiments is to force production of human G-CSF, an anti-apoptosis factor, by human MSCs. Our previous studies and the literature show that this factor is otherwise poorly produced (Haynesworth, et. al (1996), Journal of Cellular Physiology, 166 (3): 585-592). We sought to accomplish this by introducing transfecting the gene for the human G-CSF into these cells under the control of a constitutive promoter, such as CMV promoter.

hMSC were transfected by using commercially available transfecting reagents: Lipofectamine LTX™, Stemfect™ and Stemfect™ hES transfectant. A plasmid containing the popular EGFP reporter gene under the control of CMV promoter was chosen to monitor transfection efficiency by scoring for green cells under fluorescent microscopy and cytometry.

First, by excluding or replacing the media components and manipulating transfection procedure we optimized the transfection protocol and achieved the high transfection efficiencies (percentage of transfected cells) for each of the transfection reagents.

Cells were seeded and grown to about 50% confluency in standard growth media (DMEM with 15% BGS, ITS, 10 ngs/ml bFGF, 40 ng/ml Heparin). The media was removed and replaced with 1 ml low serum medium without additives (D MEM+ITS+2% BGS) and incubated overnight. The cells were transfected according to vendor recommendations. For Lipofectamine LTX, 1 ug DNA (at varying reagent/DNA ratios) was used for each well in a 12-well plate. For Stemfect and Stemfect hESC, 6 ug of DNA (at varying reagent/DNA ratios) was used.

Figure 2A:
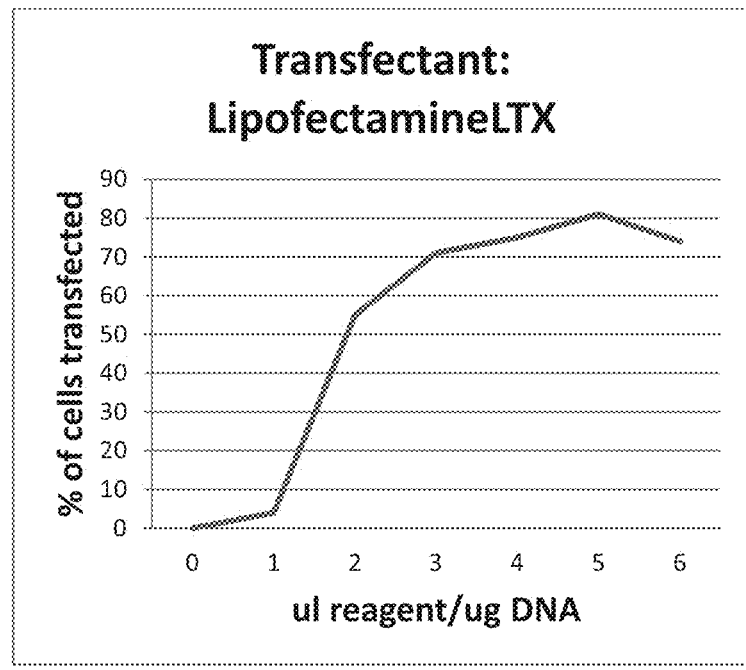
FIGS. 2A-C show the expression of an exogenous polynucleotide by transgenic mesenchymal stem cells
Figure 2B:
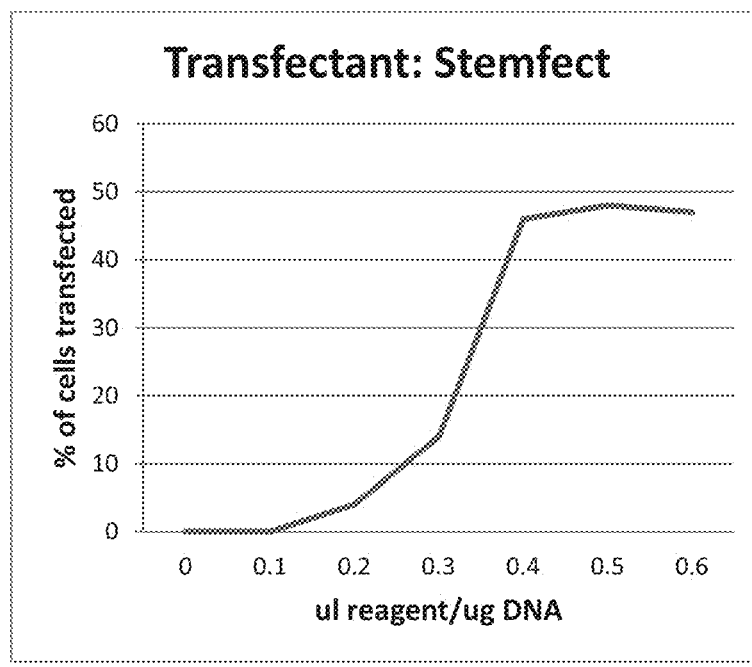
Figure 2C:
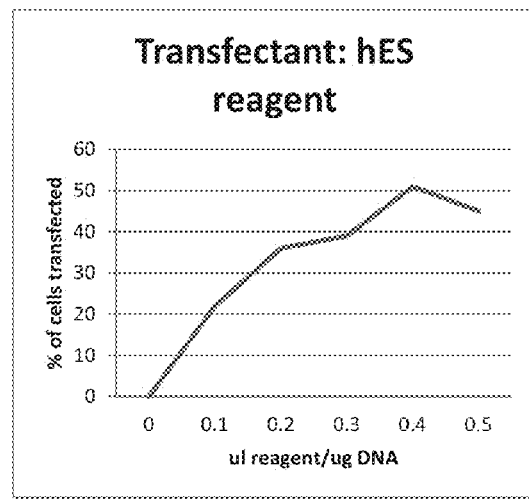

FIGS. 2A-C show the percentage of GFP positive cells transfected according to the above protocols plotted against the amount of transfection reagents.

An increase in percentage of transfected cells with increasing amount of transfecting agent for a given amount of DNA up to a point, whereupon it tends to reach a plateau. However, higher levels of transfecting agents are also toxic to cells. Hence we needed to balance transfection efficiency and cytotoxicity.

Example 3

Stem Cells Transduction

An adenoviral vector capable of expressing human G-CSF under the control of CMV promoter was constructed by standard recombinant DNA technology. This vector was converted to infective adenoviral particles by transfection of 293 human embryonic kidney cell line and subsequent lysis of these cells. The viral particles were amplified as needed by further transduction of 293 cells.

hMSCs were transduced by incubating in DMEM without serum plus an appropriate amount of amplified viral suspension for 5 hours. Bovine Growth Serum was added such that it represented 15% of total final volume and further cultured overnight. The viral suspension generally made up 10% of final volume. The cells were washed and harvested the next day, seeded on culture plates and expression of human G-CSF evaluated.

Figure 5:
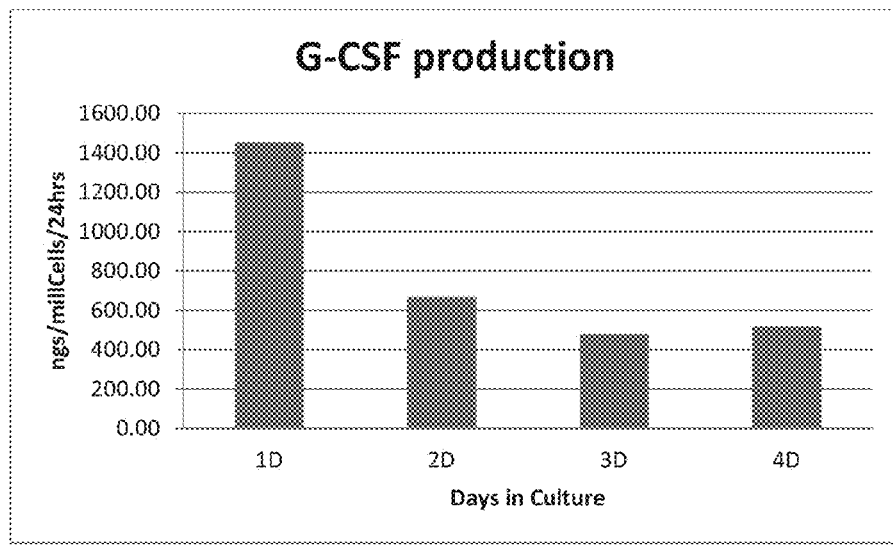
FIG. 5 shows the expression of human G-CSF by transgenic mesenchymal stem cells.

FIG. 5 shows the expression of human G-CSF over 4 days. As can be seen, transduced hMSCs secrete substantial amounts of this protein.

Example 4

In Vivo Study of Transgenic Stem Cells

The objective of this study was to investigate whether intra-arterial treatment with hMSC transduced to secrete GCST 24 hr after occlusion provides better sensory-motor recovery in rats subjected to 45 min transient middle cerebral artery occlusion (tMCAO) compared to non-transduced hMSC.

Seven-point neuroscore and amphetamine induced rotation tests were performed to study sensory-motor deficits and general condition on days 1, 3, 7 and 14 post-ischemia. After optional ex vivo MRI, brains were cryoprotected, frozen on liquid nitrogen and stored at −80° C. for possible further analysis.

Materials and Method

Animals

All animal experiments were carried out according to the National Institute of Health guidelines for the care and use of laboratory animals, and approved by the State Provincial Office of Southern Finland. Altogether 60 adult male rats, purchased from Charles River Laboratories (Sulzfeld, Germany), and weighing 250-300 g were used for the experiment. Animals were housed at a standard temperature (22±1° C.) and in a light-controlled environment (lights on from 7 am to 8 pm) with ad libitum access to food and water.

Animals were grouped as follows:
a) 15 rats treated with Vehicle, (HBSS, 2 ml/kg, i.a.) at 24 hours post-occlusion
b) 15 rats treated with non-transduced hMSC-LO2 ($2\times10^6$ cells, 2 ml/kg, i.a.) at 24 hours post-occlusion
c) 15 rats treated with G-CSF transduced hMSC-LO2 ($2\times10^6$ cells, 2 ml/kg, i.a.) at 24 hours post-occlusion Stem Cell Storage and Preparation for the Study:

Frozen stocks of transduced and non-transduced hMSC were used. On the day of injection, the cells in cryovials were thawed at 37 C and transferred to a test tube. HBSS was added slowly so as to prevent osmotic shock and lysis of cells. The tubes were centrifuged to and the cell pellet suspended in HBSS such that the cell concentration was $4\times10^6$ per ml.

Cell Delivery 24 h hours after occlusion the rats were shortly anesthetized by isoflurane and hMSC or vehicle infused intravenously (femoral vein).

Transient MCAO

Transient focal cerebral ischemia was produced by MCA occlusion in male SHR rats according to Koizumi with modifications (Koizumi et al. Jpn. J. Stroke 8:1-8, 1986). The rats are anesthetized with 5% isoflurane (in 70% N2O and 30% O2; flow 300 ml/min). During the operation the concentration of anesthetic is reduced to 1.0-1.5%. The rectal temperature is maintained at 37.0±1.5° C. with a homeothermic blanket system. After midline skin incision, the right common carotid artery (CCA) is exposed, and the external carotid artery (ECA) is ligated distal from the carotid bifurcation. A 0.25-mm diameter monofilament nylon thread, with tip blunted, is inserted 22-23 mm into the internal carotid artery (ICA) up to the origin of MCA. After 45 min of ischemia, the MCA blood flow is restored by removal of the thread. The wound is closed, disinfected, and the animals are allowed to recover from anesthesia. The rats are carefully monitored for possible post-surgical complications after the tMCAO. The rats were carefully monitored for possible post-surgical complications after the tMCAO. The rats were fed with standard laboratory diet suspended in tap water on days 0-7 after the tMCAO. To prevent dehydration all rats are given an i.p. injection of saline (4 ml per rat) once-a-day for 7 days.

Body Weight

The body weight of each animal is measured before the tMCAO and at days 1, 3, 7, and 14.

Behavioral Testing

Seven Point Neuroscore

A seven-point neuroscore test was used to assess post-ischemic motor and behavioral deficits (modified from Zausinger et al., 2000. Brain Res. 863:94-105,). The neurological test was conducted by blinded investigator at pre-MCAO (baseline) and 1, 3, 7, and 14 days after tMCAO.

Grade 6: Normal extension of both forelimbs towards the floor when lifted gently by the tail Grade 5: Consistent flexion of the forelimb contralateral to the injured hemisphere, varying from mild wrist flexion and shoulder adduction to severe posturing with full flexion of wrist, elbow, and adduction with internal rotation of the shoulder.

Grade 4: Dysfunctional rats with a consistently reduced resistance to lateral push towards the paretic side.

Grade 3: Rats circling towards the paretic side if pulled and lifted by the tail.

Grade 2: Rats circling towards the paretic side if pulled by the tail.

Grade 1: Rats circling spontaneously towards the paretic side.

Grade 0: Rats with no spontaneous motion

Statistical Analysis

All values are presented as mean±standard deviation (SD) or standard error of mean (SEM), and differences are considered to be statistically significant at the P<0.05 level. Statistical analysis is performed using StatsDirect statistical software. Differences among means are analyzed by using 1-way-ANOVA followed by Dunnet's test (comparison to the control (=vehicle treated aged rats) group). Within-group comparison to the baseline is done by 2-way-ANOVA. Non-parametric data is analyzed with Kruskal-Wallis ANOVA or Friedman ANOVA, respectively.

Biodistribution of transduced and non-transduced HBMSC was determined by labeling them with Indium. 3 rats per group were injected I.V. with 2 million cells each in a volume of 0.5 ml. Their distribution in vivo was followed by SPECT/CT imaging and tissue distribution ascertained by gamma counting. Briefly, the cells were incubated with 4.76-5.65 MBq$^{111}$ in-oxine in Tris-buffer for 30 min, after which the cells were washed once to remove free tracer and then resuspended in HBSS for transplantation. SPECT imaging of the brain and abdomen was performed with a small animal SPECT/CT. The animals were sacrificed and various tissue extracted for gamma counting.

Results

Figure 6:
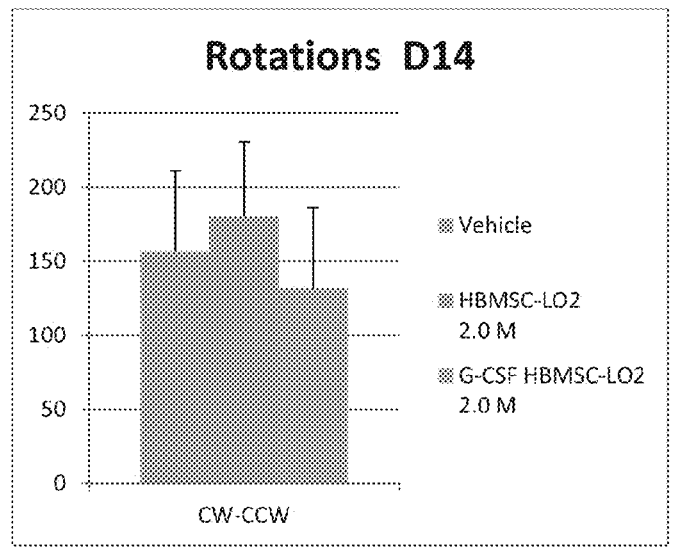
FIG. 6 shows the results obtained for rotation tests performed on adult TMACO rats treated with human transgenic G-CSF mesenchymal stem cells.
Figure 7:
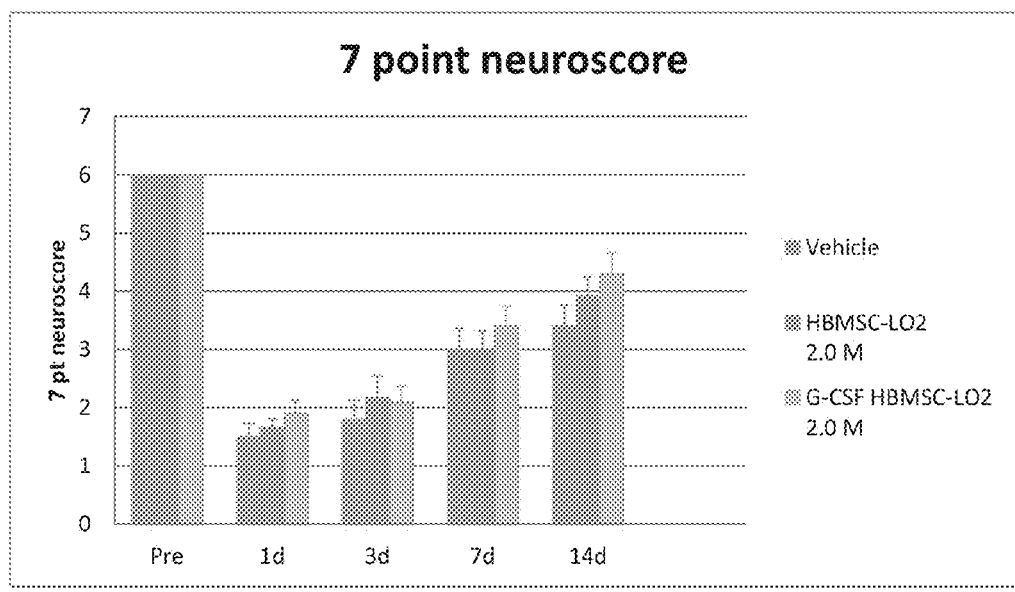
FIG. 7 shows the results obtained for 7 point neuroscore performed on adult TMACO rats treated with human transgenic G-CSF mesenchymal stem cells.

Both rotation tests (FIG. 6) and 7-point neuroscore (FIG. 7) reveal better recovery of the animals from stroke induced deficiencies when treated with G-CSF producing hMSC.

Figure 8A:
FIGS. 8A-C show the biodistrution of administered mesenchymal stem cells.
Figure 8B:
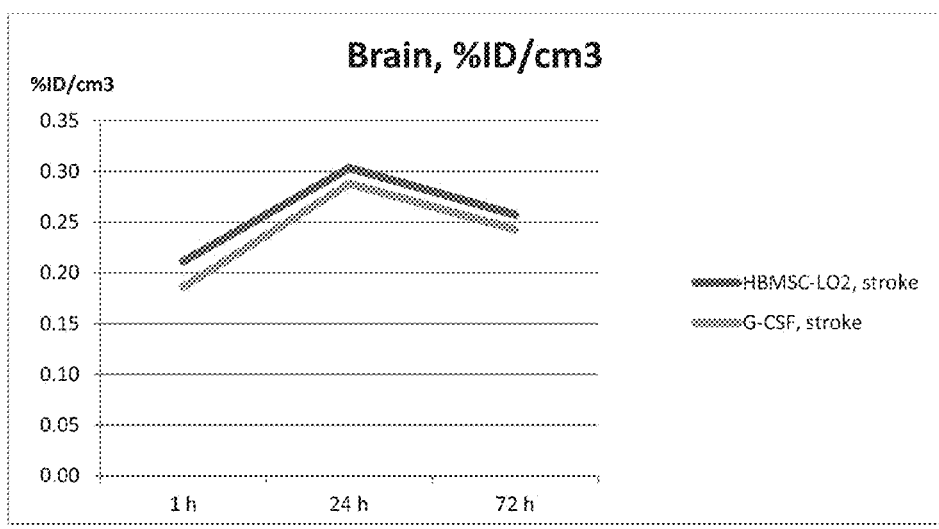
Figure 8C:
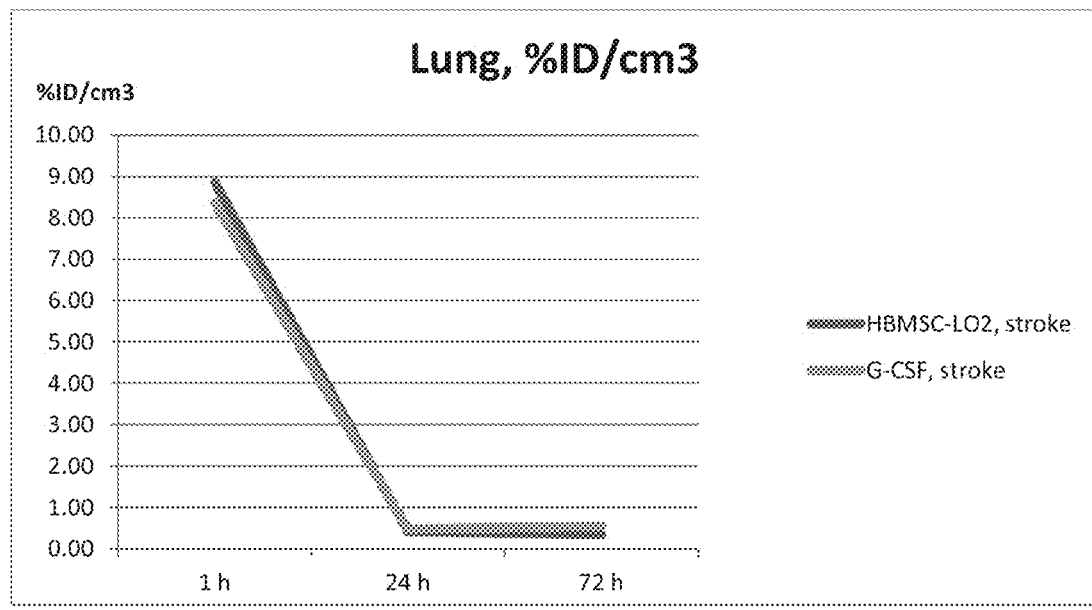

The biodistribution of hMSC in these animals did not reveal any differences, indicating that these genetically altered cells have similar migratory properties in vivo (FIGS. 8A-C).

We claim:

1. A transgenic in vitro mesenchymal stem cell, said stem cell comprising a transiently expressed exogenous polynucleotide sequence encoding G-CSF (granulocyte colony-stimulating factor) introduced into said stem cell from adenovirus or a plasmid comprising said polynucleotide sequence encoding G-CSF, said mesenchymal stem cell having a doubling time of about 23 hours under hypoxic conditions wherein said mesenchymal stem cell is positive for CD13, CD29, CD73, CD81, CD90, CD105, CD164 and CD166, and negative for CD14, CD19, CD34, CD45, CD122 and HLA-DR wherein said transgenic cell is derived from mesenchymal stem cells obtained from bone marrow and grown under low oxygen conditions.

* * * * *